United States Patent [19]

Anouchi et al.

[11] 4,447,397
[45] May 8, 1984

[54] CATALYTIC GAS SENSOR

[75] Inventors: Abraham Y. Anouchi, Aspinwall; Robert L. Novack, Evans City; Beth Tomasovic, Butler, all of Pa.

[73] Assignee: Bacharach Instrument Company, Pittsburgh, Pa.

[21] Appl. No.: 405,449

[22] Filed: Aug. 5, 1982

[51] Int. Cl.³ ............................................. G01N 27/16
[52] U.S. Cl. .......................................... 422/94; 73/23; 338/34; 422/95; 422/97; 436/127; 436/142
[58] Field of Search ................................. 422/94–98; 436/152; 73/23, 27 R; 340/633–634; 338/34

[56] References Cited

U.S. PATENT DOCUMENTS

| | | | |
|---|---|---|---|
| 3,092,799 | 6/1963 | Baker | 338/34 |
| 4,045,177 | 8/1977 | McNally | 422/96 |
| 4,068,021 | 1/1978 | Allman | 422/83 X |
| 4,355,056 | 10/1982 | Betta et al. | 338/34 X |

Primary Examiner—Michael S. Marcus
Assistant Examiner—Michael S. Gzybowski
Attorney, Agent, or Firm—Harry J. Gwinnell

[57] ABSTRACT

A reference element for a catalytic gas sensor with improved life in the presence of combustible gases is described. The sensor comprises a filament such as a platinum-iridium alloy coated with a layer of titanium dioxide. The coating typically contains a high temperature stable inorganic binder such as aluminum oxide. The filament can be in coil-form pre-encased in a glass bead. Such sensor has long term stability in the presence of combustible organic gases such as alkenes, alkadienes, alkynes, and epoxide containing hydrocarbon gases, for example. Sensors containing such elements have particular utility in the area of mining and oil drilling environments, as well as industrial, safety, and commercial applications.

3 Claims, 3 Drawing Figures

CATALYTIC GAS SENSOR

DESCRIPTION

1. Technical Field

The field of art to which this invention pertains is the detection of gaseous impurities in air, and specifically the detection of combustible gases utilizing heated catalytic and non-catalytic elements.

2. Background Art

Although catalytic gas sensors have been available for many years, there has been an on-going attempt to improve their performance. Basically, these sensors work by using a catalyst on a filament (or a catalytic filament e.g. platinum) which, when heated, causes the oxidation of a combustible gas in air. When heating from such oxidation takes place, the electrical resistance of the thus heated filament changes. A second element, called a reference element, is also subjected to the same environment as the first element and is sensitive to such conditions as pressure, temperature, humidity, etc. but is non-catalytic or relatively passive to the combustible gas. The two filaments are usually connected as part of a Wheatstone bridge electrical circuit. The electrical resistance imbalance caused by the burning is measured on a meter calibrated to detect the percentage of combustible gases in the air being sampled.

In the case of detecting some organic gases, such as epoxides and other hydrocarbon gases such as alkenes, alkadienes, alkynes, etc. because of their high reactivity toward burning, standard non-catalytic reference element coatings such as alumina silicate and silica based coatings become active in the burning process. Sensors exposed to the above type gases become insensitive after a few hours of use. When detecting for such gases, it is therefore necessary to change such sensors after only a few hours of exposure.

Accordingly, what is needed in this art is a reference element for detecting organic gases with improved durability.

DISCLOSURE OF INVENTION

An improved reference element for a catalytic gas sensor with improved life and durability is disclosed which comprises an electrically conductive filament coated with a layer of titanium dioxide. Such reference element remains non-catalytic and relatively passive to the burning of combustible gases including organic gases such as unsaturated hydrocarbons and epoxies providing a catalytic gas sensor with prolonged life and improved sensitivity.

Another aspect of the invention includes a catalytic gas sensor particularly adapted to detecting the presence of organic gases. The sensor comprises an element catalytically active toward the presence of combustible gases including organic gases and a passive reference element as described above.

Another aspect of the invention includes a catalytic gas detecting instrument particularly adapted to detecting the presence of organic gases. The instrument is made up of an element catalytically active toward the presence of combustible gases including organic gases, a passive reference element as described above, a power source, and audio or visual means particularly adapted to measuring electrical imbalances between the active and passive elements.

The foregoing, and other features and advantages of the present invention, will become more apparent from the following description and accompanying drawing.

BEST MODE FOR CARRYING OUT THE INVENTION

Figure 3:
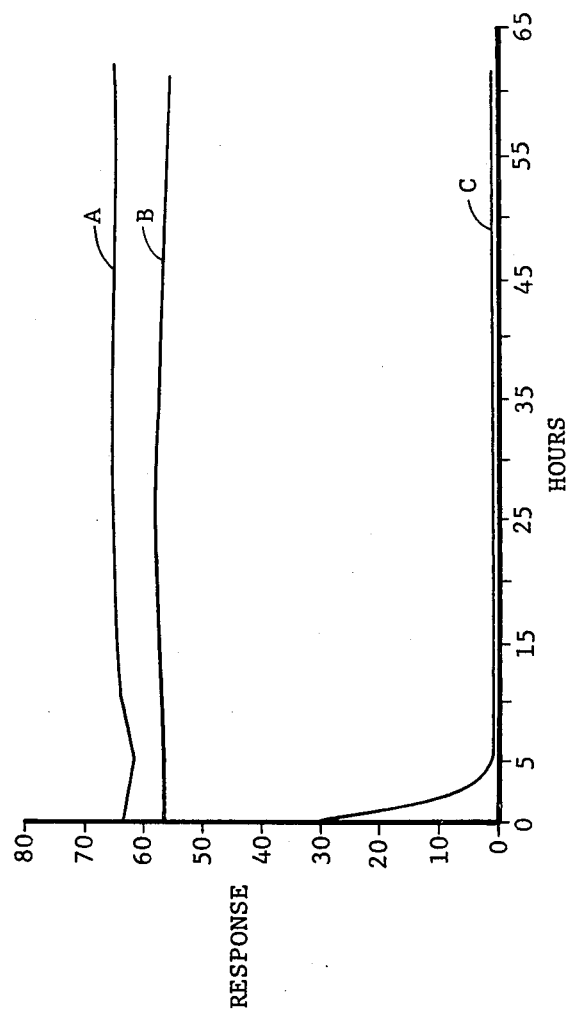
FIGS. 2 and 3 show graphically the performance of reference elements of the present invention as compared to elements of the prior art.

The filament used for the passive element can be the same as or different than that used for the active element and generally comprises a noble metal such as platinum, or an alloy of such metal to provide increased strength and handleability to the noble metal. Platinum alloys such as platinum-rhodium, platinum-iridium, platinum-ruthenium, platinum-gold, etc. can be used. If a platinum alloy is used, the platinum should be present in at least about 80% by weight. The filament generally has a circular cross-section and diameter of 0.5 to 10 mils, and preferably about 1.0 to 2.0 mils. The filament should have a resistance per unit length compatible with the amount of power supply voltage available and have a significant alpha, i.e. thermal coefficient of resistance. A spool of filament wire can be commercially purchased with an aluminum oxide insulation coating of sufficient thickness to provide electrical insulation while still imparting formability to the wire. Although it is preferred to use a coil form for best performance, to minimize radiational heat losses and maximize power consumption efficiency, any form desired and even straight filament form may be used.

If a coil form is used, the coil is formed with enough turns to make the sensor compatible with the power supply used, typically with 4 to 8 turns with an overall coil diameter of about 10–20 mils. The filament can be coated directly with the titanium dioxide coating although more typically the filament in coil form is encased in a conventional glass bead (well-known in this art) and the titanium compound applied to the glass bead.

The titanium compound coating can be applied in one thick coating but is preferably applied in a series of coatings to ensure a layer which is gas impermeable. The coating is typically about 1 to about 2 mils thick.

The titanium compound used should be in finely powdered form. Although it is preferred to use commercial pigment grade titanium dioxide, any titanium compound which will oxidize or decompose to form titanium dioxide can also be used, such as titanium carbide. This material can also be either purchased commercially or made by conventional methods. The titanium carbide or titanium dioxide powder is applied to the coil, preferably in slurry form. This can be done with a brush, needle, pin, spatula, wire loop, wooden stick, toothpick, etc. And while the titanium carbide or titanium dioxide can be applied alone, it is preferably applied with an inorganic binder. The use of the binder provides the obvious advantage of better adhesion of the titanium carbide or titanium oxide to the wire. The preferred binder is aluminum nitrate but any inorganic binder which is ultimately stable at the temperatures the sensors will reach, can be used, such as sodium silicate for example. If a platinum catalyst is being used, the binder should be ultimately stable at temperatures of the order of 600° C.-900° C., paladium at 400° C.-700° C., etc. By ultimately stable is meant unchanging in form at such temperature. For example, the aluminum nitrate is ultimately stable as aluminum oxide at such temperature, the sodium silicate is ultimately stable as dehydrated sodium silicate etc. While a binder is not necessary, practically it is important to prevent chipping and flaking of the TiO$_2$ coating.

Once applied, the slurry can be dried by either external heating, or by resistance heating, simply by passing electric current through the filament. At this time if TiO$_2$ is not used as the starting material the titanium compound is oxidized and becomes essentially titanium dioxide. If the titanium compound or titanium dioxide is mixed with a binder such as aluminum nitrate or other inorganic material, the binder is generally present in amounts of about 2% to about 10% by weight in its final ultimately stable heat treated form (e.g. Al$_2$O$_3$ for aluminum nitrate), based on weight of TiO$_2$ plus binder. Sufficient carrier (e.g. water) is present in the slurry to allow the slurry to be easily applied to the filament or glass bead encased filament with a coating tool such as described above.

EXAMPLE 1

Figure 1:
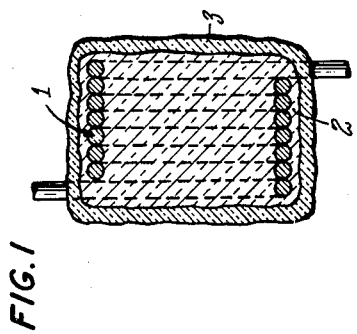
FIG. 1 shows a typical reference element coated according to the present invention.

One gram of titanium carbide powder of −325 mesh is placed in a 10 ml vial. 20 drops of an aqueous solution of 40% by weight aluminum nitrate is added to the titanium carbide. The mixture is stirred to form a uniform slurry. Several turns of a coil of platinum-iridium alloy having a wire diameter of one mil are coated with sufficient alumina to prevent shorting. A slurry of glycerine and powdered glass (Corning 1715) is applied to completely encase the coil, which is then resistance heated to dry and melt and form a protective glass bead. To this bead is applied several coats of the titanium carbide slurry which are also dried and bonded. The entire element is then heated until an essentially steady state crystalline form of TiO$_2$ is attained, as detected, for example, by an essentially zero-draft test response of the element in air. Typically this occurs within about 48 to about 200 hours. The voltages and times for resistance heating are conventional in this art and are determined by the size of the wire or coil, amount and type of coating material applied and projected operating of the sensor. A typical, thus coated coil is shown in FIG. 1 where 1 is the coil, 2 is the glass bead and 3 the TiO$_2$ coating.

EXAMPLE 2

The same procedure described in Example 1 is repeated, except for replacing the titanium carbide with titanium dioxide.

Figure 2:
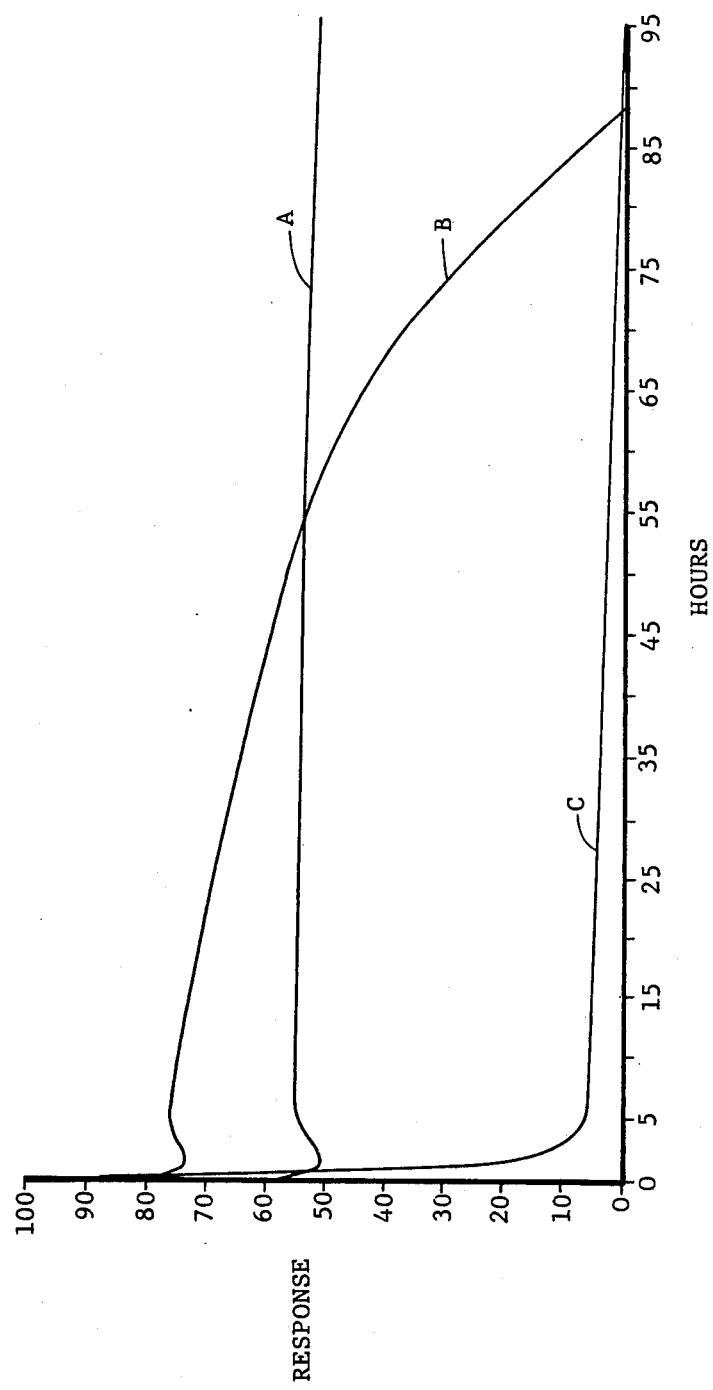

A standard commercially available 6 volt, 2 mil wire gas sensors where the reference element is coated with a standard sodium silicate solution (curve C) was tested under similar conditions against the same 6 volt, 2 mil wire sensor with a reference element coated with two coats (2 mils) of titanium dioxide (curve A) and titanium carbide (curve B) as described above. As seen in FIG. 2, where Wheatstone bridge imbalance (i.e. output or response) is plotted as a function of time, the titanium dioxide maintained level performance even after 95 hours, whereas the sodium silicate showed significant drop-off after only 5 hours, and the titanium carbide began to show significant drop-off after about 65 hours. The drop-off in Curve B can even be improved by applying a thicker TiC coating or more layers of TiC. It should be noted that other means of measuring the electronic imbalance of the elements in the sensor may be used besides the Wheatstone bridge, such as direct reading or advanced signal processing using microprocessor electronics. The power source for the gas detecting instrument may be internal or external to the instrument. The meter means used to measure the electrical imbalance can also be either audio or visual and an analog or digital read out (or both). The test gas here was air containing 1.6% by volume 1,3 butadiene.

In a similar test, as shown in FIG. 3 using the same 6 volt, 2 mil sensor, similar results were observed for the sodium silicate coated reference element (curve C), but both the titanium dioxide (curve A) and the titanium carbide (curve B) coated reference elements showed maintenance of sensor quality even after 60 hours of testing. Here the titanium dioxide coating was applied in one layer whereas the titanium carbide coating was applied in 4 layers.

Although testing is shown here for butadiene, other easily oxidized organic gases such as alkenes, alkadienes, alkynes and epoxide containing hydrocarbon gases can be tested with similar results. As shown not only is the life of the sensor increased but the sensitivity of the sensor is more constant over the life of the sensor. Such sensors can be used with personal gas sensing instruments, area gas sensing instrument, and system gas sensing equipment. This has particular utility in various mine, industrial, safety, and commercial environments.

Although this invention has been shown and described with respect to detailed embodiments thereof, it will be understood by those skilled in the art that various changes in form and detail thereof may be made without departing from the spirit and scope of the claimed invention.

We claim:

1. A reference element for a catalytic gas sensor comprising an electrically conductive filament coated with an electrically insulating first layer of Al$_2$O$_3$, a second layer of titanium dioxide coated upon said first layer and containing inorganic binder, the inorganic binder representing up to about 10% by weight of the second layer and the balance being titanium dioxide, said filament coated with said first and second layers being encased in a glass bead so as to produce a reference element with improved life and durability.

2. A catalytic gas sensor particularly adapted to detecting the presence of combustible organic gases in air, comprising an element catalytically active in the presence of each organic gases, and an element catalytically passive in the presence of such organic gases, wherein the improvement comprises utilizing as the passive element, an electrically conductive filament coated with an electrically insulating first layer of Al$_2$O$_3$, a second layer of titanium dioxide coated upon said first layer and containing inorganic binder, the inorganic binder present in an amount up to about 10% by weight of the second layer and the balance of the second layer being titanium dioxide, said filament coated with said first and second layers encased in a glass bead so as to produce a catalytic gas sensor with improved life and durability.

3. A catalytic gas sensing instrument particularly adapted to detecting the presence of combustible organic gases in air, comprising an element catalytically active in the presence of such organic gases, a coated element catalytically passive in the presence of such organic gases, a power source providing electrical current to the active and passive elements, and an audible or visual means particularly adapted to measuring the electrical imbalances between the active and passive elements, wherein the improvement comprises utilizing as the passive element, an electrically conductive filament coated with an electrically insulating first layer of $Al_2O_3$, a second layer of titanium dioxide coated upon said first layer and containing inorganic binder, the inorganic binder being present in an amount up to about 10% by weight of the second layer and the balance of the second layer being titanium dioxide, said filament coated with said first and second layers encased in a glass bead so as to produce a sensing instrument with improved life and durability.

* * * * *